United States Patent [19]
Gibson et al.

[11] Patent Number: 5,457,190
[45] Date of Patent: Oct. 10, 1995

[54] PROCESS FOR THE PREPARATION OF GLYCOSIDES

[75] Inventors: Michael W. Gibson, Fairfield, Ohio; Patrick M. McCurry, Jr., Lansdale, Pa.; Carl E. Pickens, Hamilton, Ohio

[73] Assignee: Henkel Corporation, Plymouth Meeting, Pa.

[21] Appl. No.: 891,305

[22] Filed: May 29, 1992

[51] Int. Cl.$^6$ .............................. C07H 15/04; C07H 1/00
[52] U.S. Cl. ........................ 536/18.6; 536/18.5; 536/120
[58] Field of Search .................... 536/18.6, 18.5, 536/120

[56] References Cited

U.S. PATENT DOCUMENTS

| | | | |
|---|---|---|---|
| H619 | 4/1989 | McDaniel et al. | 536/18.5 |
| 3,219,656 | 11/1965 | Boettner | 536/18.6 |
| 3,839,318 | 10/1974 | Mansfield | 536/18.6 |
| 4,721,780 | 1/1988 | McDaniel et al. | 536/18.6 |
| 4,939,245 | 7/1990 | Rasche et al. | 536/18.6 |
| 4,950,743 | 8/1990 | McCurry et al. | 536/18.6 |
| 5,003,057 | 3/1991 | McCurry et al. | 536/18.6 |

FOREIGN PATENT DOCUMENTS

| | | |
|---|---|---|
| 272247 | 1/1967 | Australia . |
| 0132046 | 4/1988 | European Pat. Off. . |
| 3833780 | 5/1988 | Germany . |

*Primary Examiner*—Michael G. Wityshyn
*Assistant Examiner*—Everett White
*Attorney, Agent, or Firm*—Ernest G. Szoke; Wayne C. Jaeschke; Daniel S. Ortiz

[57] ABSTRACT

A process for preparing aliphatic polysaccharides in which a slurry of a hydrous saccharide source in a first portion of aliphatic alcohol is introduced into a second portion of the aliphatic alcohol maintained at an elevated temperature and under a reduced pressure to form a mixture of saccharide source and alcohol with a reduced water content, introducing an acid catalyst into the mixture with the reduced water content and reacting the aliphatic alcohol with the saccharide source to form an aliphatic glycoside.

15 Claims, 1 Drawing Sheet

PROCESS FOR THE PREPARATION OF GLYCOSIDES

BACKGROUND OF THE INVENTION

Aliphatic glycosides have been known for at least sixty years. They are nonionic surfactants with low toxicity and gentleness to the skin. They can be made from renewable resources and are rapidly degraded in the environment.

In spite of the excellent properties of the aliphatic glycosides, they have not achieved great commercial acceptance because of the difficulties encountered in their production. Rohm & Haas Corporation has been providing alkyl glycosides in which the alkyl group is formed from a mixture of fatty alcohols having 8 and 10 carbon atoms. The compositions were sold under the trade name BG-10 and CG-110. The BG-10 composition is a dark, almost black, material and is used only in commercial formulations. The CG-110 material is a light colored product having a dissolved solids content of about 70%, which is useful for consumer applications.

Early processes for the preparation of aliphatic glycosides were two-step processes. The first step comprised the reaction of a lower alcohol having 1 to 6 carbon atoms with a source of saccharide in the presence of an acid catalyst to form the aliphatic glycoside. These aliphatic glycosides do not have useful surfactant properties. Since water is miscible with, or highly soluble in, the alcohols, the reaction mixture can contain substantial quantities of water (see U.S. Pat. No. 4,721,780). The higher aliphatic glycosides in which the aliphatic group contains from 7 to 22 carbon atoms, were prepared by transacetalization of the lower glycosides with higher fatty alcohols under substantially anhydrous conditions.

More recently, aliphatic glycosides having alkyl groups with from 7 to about 22 carbon atoms have been prepared by a "direct process". In the "direct process" a long chain fatty alcohol is reacted with a source of saccharide in the presence of an acid catalyst under conditions in which the water formed in the reaction is removed as quickly as it is formed to maintain the water content of the reaction mixture at as low a level as is reasonably possible. The water formed in the reaction is only slightly soluble in the fatty alcohol and any undissolved water results in the rapid formation of unwanted byproducts. The parameters of the "direct process" were set out in U.S. Pat. No. 3,839,318, which is incorporated herein by reference. Other patents such as U.S. Pat. Nos. 4,939,245, 4,950,743 and 5,003,057 also describe the "direct process" and are incorporated herein by reference.

The references disclose use of an anhydrous source of saccharide or mixing a hydrous saccharide source with an alcohol, present in stoichiometric excess, and heating the mixture under reduced pressure to remove the water. An acid catalyst is added to the mixture of saccharide source and fatty alcohol after the water has been substantially eliminated and the mixture heated under reduced pressure to form the aliphatic glycoside (see Australian patent 272,247 and EP 132 046). German application 3 833 780.0 discloses forming a slurry of anhydrous saccharide and alcohol and adding the slurry to a heated second portion of alcohol.

It is preferred to use a hydrous saccharide source since hydrous saccharide sources are much less expensive than the anhydrous material.

BRIEF DESCRIPTION OF THE INVENTION

According to the invention, an improved process for preparing an aliphatic glycoside is provided which comprises providing a zone containing a second portion of fatty alcohol at an elevated temperature and under a reduced pressure and introducing a slurry comprising a first portion of fatty alcohol and a hydrous saccharide source into the heated second portion of fatty alcohol in a controlled manner, either incrementally or continuously.

The mixture of hydrous saccharide source and first portion of alcohol is introduced into the heated second portion of alcohol to form a mixture at a rate such that the temperature of the second portion of alcohol is not substantially reduced and the source of vacuum can maintain the required reduced pressure. After the introduction of the mixture of first portion of alcohol and hydrous saccharide source into the second portion of alcohol, the mixture may be heated further as required until the water has been reduced to the required level.

The hydrous saccharide source is not a liquid, but a solid which contains water. Saccharide sources such as dextrose monohydrate, solidified high dextrose corn syrup, and the like are suitable.

The mixture of hydrous saccharide source and first portion of alcohol can be warmed before introduction into the heated second portion of alcohol under reduced pressure as long as the temperature of the mixture is maintained below the syrupification point of the hydrous saccharide source and the hydrous saccharide source is introduced into the heated second portion of alcohol as a slurry of a solid material in fatty alcohol.

BRIEF DESCRIPTION OF THE DRAWINGS

The FIGURE is a diagrammatic representation of a reaction system useful in the practice of the invention.

DETAILED DESCRIPTION OF THE INVENTION

Figure 1:
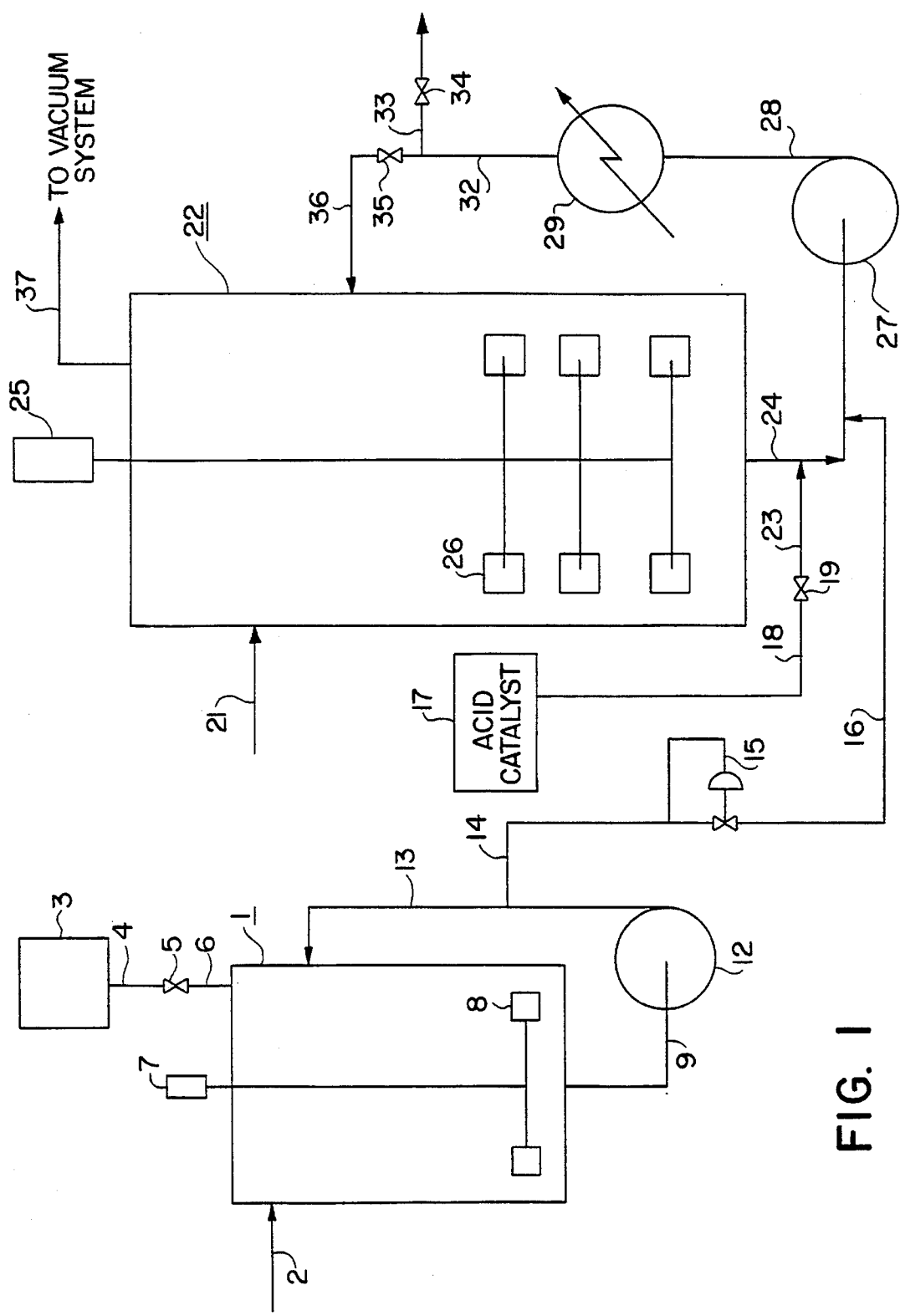

The term "fatty alcohol" as used herein refers to aliphatic alcohols having from about 7 to about 22 carbon atoms. The alcohol may be represented by the formula

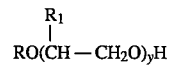

wherein R is the residue of a fatty alcohol containing from about 7 to 22 carbon atoms, $R^1$ is H, $CH_3$ or $-CH_2-CH_3$ and Y is a number from 0 to about 5. The alcohols can be saturated or unsaturated, straight chain or branched chain. The fatty alcohol used in the process of the invention can be a single alcohol or a mixture of alcohols. Preferably, the fatty alcohols are aliphatic alcohols having from 8 to about 18 carbon atoms. Alcohols having aromatic or other cyclic moieties in their structure can also be reacted but the glycosides formed are generally not as biodegradable as the glycosides formed from aliphatic alcohols.

As used herein, a "hydrous saccharide source" refers to a reducing sugar or an oligomer or polymer comprising moieties of a reducing sugar which under the acid conditions of the process forms a reducing saccharide required to react with the alcohol. The term "hydrous" refers to a solid saccharide source which contains water. Materials such as dextrose monohydrate, solidified high dextrose corn syrup and the like have been found useful to prepare the aliphatic glycosides by the improved process of the invention.

The term "aliphatic glycoside" is used to denote a composition of the formula

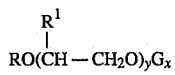

$$RO(\overset{R^1}{\underset{|}{C}H}-CH_2O)_y G_x$$

wherein R is the residue of a fatty alcohol having from about 7 to about 22 carbon atoms; $R^1$ is H, $CH_3$ or $CH_2CH_3$, G is the residue of a reducing saccharide; y is an average number of from 0 to about 5; and x is an average number of from 1 to about 5. Preferably x is a number of from 1 to about 2.5.

G is the residue of a reducing saccharide. The residue of a reducing saccharide can be the residue of a monosaccharide such as glucose, fructose, lactose, mannose, xylose and the like or the residue or fragments of a polysaccharide or oligosaccharide such as sucrose, maltose, maltotriose, cellobiose, mellobiose and the like. The oligosaccharides break down under the acid conditions and elevated temperature of the process to produce the reducing saccharide moieties which react with the alcohol.

The source of saccharides useful in the practice of the present invention are hydrous materials; that is, they are solids which contain water. The water may be in the form of water of crystallization or merely water which has been adsorbed on the surface of the saccharide source. Materials such as dextrose monohydrate which contains one molecule of water for each saccharide unit, and solidified high dextrose corn syrup are useful in the practice of the invention.

The method of the present invention is not particularly suitable for utilizing a hydrous saccharide source which is a liquid. It is difficult to prepare an adequate suspension of the liquid in a portion of the alcohol and introduce the suspension into the heated second portion of alcohol without causing the source of saccharide to become sticky and cling to the surfaces, especially in the zone in which the water is being removed from the mixture of the saccharide source and fatty alcohol.

The hydrous saccharide source is mixed with a first portion of the fatty alcohol. The first portion of the fatty alcohol generally is less than 50% of the amount of the first and second portions of fatty alcohol. Generally, the first portion of the fatty alcohol is from about 20 to about 40% of the amount of the first and second portions of alcohol. The fatty alcohol is always present in stoichiometric excess during the reaction.

The second portion of the fatty alcohol which is heated and under a reduced pressure generally comprises more than about half of the alcohol present in the reacting mixture. Preferably, the second portion of fatty alcohol comprises from about 60 to about 80% by weight of the total amount of fatty alcohol which is present in the reacting mixture. The fatty alcohol present in the reacting mixture ranges from more than 1 mole of fatty alcohol per mole of the reducing saccharide residue to a practical limit of about 15 moles of fatty alcohol per mole of reducing saccharide residue. Preferably, the amount of fatty alcohol in the reacting mixture ranges from about 1.5 moles to about 8 moles and most preferably from about 2 to about 7 moles of fatty alcohol per mole of reducing saccharide residue.

The ratio of fatty alcohol to reducing saccharide residue is generally maintained at a point at which the reacting mixture has sufficient fluidity so that it can be adequately heated, pumped and stirred to keep the undissolved source of saccharide in suspension and to permit the water formed in the reaction to be rapidly removed from the reacting mixture. Preferably from about 2 moles of fatty alcohol per mole of saccharide residue to about 6 moles of fatty alcohol per mole of saccharide residue are sufficient to maintain the reacting mixture in a fluid state.

The ratio of moles of fatty alcohol to moles of reducing saccharide residue in the reacting mixture also impacts the degree of polymerization (DP) or the value of x in the aliphatic glycoside product.

During the addition of the slurry of the hydrous saccharide source to the heated second portion of fatty alcohol under reduced pressure, the temperature of the second portion of fatty alcohol is initially maintained below about 130° C. and preferably in the range of from about 60° C. to about 110° C. The temperature of the mixture of the fatty alcohol and the hydrous saccharide source is maintained intentionally low to prevent any of the hydrous saccharide source from reaching a temperature at which the hydrous saccharide source becomes a liquid or syrup before a sufficient amount of water has been removed. The temperature of the mixture is raised at a rate sufficient to remove the water but maintain the hydrous saccharide source as a solid.

The slurry of the hydrous saccharide source in the first portion of the fatty alcohol can be warmed before it is introduced into the heated second portion of fatty alcohol at the reduced pressure. However, the slurry must not be heated to a temperature above which the hydrous saccharide source becomes a liquid or syrup.

The slurry of the hydrous saccharide source in the first portion of fatty alcohol is introduced into the heated second portion of fatty alcohol, maintained under a reduced pressure, at a controlled rate. The slurry of the hydrous saccharide source can be introduced into the heated fatty alcohol at the reduced pressure incrementally or continuously and preferably continuously.

Before the slurry of hydrous saccharide source in the first portion of the fatty alcohol is introduced into the heated second portion of alcohol, the second portion of alcohol is maintained under a pressure of about 100 mm Hg or less, preferably at a pressure below about 50 mm Hg when the alcohol contains at least 10 carbon atoms. The pressure at which the second portion of alcohol is maintained is dependent upon the alcohol used in the process and is preferably in the range at which the reaction between the alcohol and saccharide source is to be carried out. The pressure is preferably in the range of from about 1 mm Hg to about 100 mm Hg, more preferably in the range of from about 5 mm Hg to about 70 mm of Hg. The reaction between the alcohol and saccharide source can be carried out in the same pressure range.

The reduced pressure is useful in reducing the amount of water in the mixture to a level at which the unwanted side reactions are low and the process is directed to formation of the aliphatic glycoside.

The amount of water in the mixture of the saccharide source and fatty alcohol is substantially reduced and when the mixture is maintained at the reduced pressure and elevated temperature the water is quickly evaporated from the mixture. A mixture of saccharide source and fatty alcohol containing an amount of water which approaches the equilibrium moisture content under the conditions of temperature and pressure is considered as substantially anhydrous. The preferred compositions generally contain less than 1% by weight water, preferably less than 0.5% by weight water. The amount of water present in the mixture depends upon the alcohol present and the temperature and pressure under which the mixture is maintained.

The rate of addition of the slurry of the hydrous saccharide source in the first portion of fatty alcohol is determined by the ability of the vacuum system to maintain a suitable reduced pressure on the system and the ability of the heating means to maintain the temperature of the heated fatty alcohol to which the slurry of the hydrous saccharide source in the fatty alcohol is introduced. If the rate of addition of the slurry of the hydrous saccharide source in the first portion of fatty alcohol into the second portion of the fatty alcohol which has been heated to a temperature in the range of from about 60° C. to about 110° C. under a reduced pressure is too high, the introduction of the cold material and the vaporization of the water can substantially reduce the temperature of the mixture of the fatty alcohol and saccharide source. In addition, the rapid release of the water from the hydrous saccharide source can overload the reduced pressure producing system (vacuum system) and cause the pressure on the mixture to increase to unacceptably high levels.

In the process of the present invention, it is preferred that the slurry of the hydrous saccharide source in the first portion of fatty alcohol be introduced into the second portion of the fatty alcohol at such a rate that the reduced pressure can be maintained in a desired range and the temperature of the second portion of the fatty alcohol can be maintained within a preselected temperature range.

The fatty alcohol in the zone in which the second portion of the fatty alcohol is heated under reduced pressure can be heated by means of a jacket on the outside of the vessel, coils inside the vessel, by circulating a stream of the fatty alcohol through an external heat exchanger, or by a combination of methods or other means known for heating liquids within processing vessels.

After the addition of the desired amount of the slurry of hydrous saccharide source and first portion of the fatty alcohol to the second portion of the fatty alcohol under reduced pressure, the mixture is heated to a temperature in the range of the reaction temperatures. The reaction between a fatty alcohol and a source of reducing saccharide is generally carried out in the range of from about 90° C. to about 140° C., and preferably in the range of from about 95° C. to about 125° C. and most preferably from about 100° C. to about 120° C. The mixture of the hydrous saccharide source in the first portion of the fatty alcohol and the second portion of the fatty alcohol is heated until the reaction temperature range is attained and the water in the mixture has been reduced to the required level. Preferably, the water is reduced to a level at which undissolved water is minimal in the reaction mixture and most preferably to a level as low as is commercially practical. All of the water cannot be removed from the mixture under any reasonable conditions and therefore a small amount of water is always present in the reacting mixture.

After the amount of water in the mixture of the first and second portions of the fatty alcohol and the hydrous saccharide source has been reduced to the required level, and the temperature of the mixture is in the reaction range, an acid catalyst is introduced into the mixture. The acid catalysts useful in the practice of the present invention are well known materials and comprise inorganic acids such as sulfuric acid, phosphoric acid, hydrochloric acid, and the like. Organic acids such as trifluoroacetic acid, paratoluene sulfonic acid, sulfosuccinic acid, cumene sulfonic acid, sulfonated fatty acids and sulfonated fatty acid esters, acid forms of surfactants such as alkyl benzene sulfonic acid, fatty alcohol sulfates, alkoxylated fatty alcohol sulfates, alkylsulfonates, alkyl esters of sulfosuccinic acid, alkyl naphthalene sulfonates wherein the alkyl group or groups contain more than a total of about 8 carbon atoms, and preferably in the range of 16 to about 32 carbon atoms, acid forms of resins and other known acid catalysts for the acetalization of reducing saccharides by fatty alcohols.

After the addition of the catalyst, the reacting mixture is well agitated and maintained at the reaction temperature in the range of from about 90° C. to about 130° C. under a reduced pressure to remove the water formed in the reaction substantially immediately as it is formed. The reaction is carried out for a sufficient length of time to react the source of saccharide present in the reaction mixture with the fatty alcohol to form the aliphatic glycoside. As is well understood in the art, the degree of polymerization (the number of glycoside residues which are polymerized and attached to an aliphatic group) is determined by: 1. structure and the excess of the fatty alcohol; 2. the amount and type of catalyst utilized; and 3. reaction time, temperature and pressure. The effect of these variables is known in the art and will not be discussed here.

As is well known in the art, the reaction between the fatty alcohol and the saccharide source under the acid conditions is carried out under sufficient agitation and reduced pressure to permit the water formed in the reaction to be rapidly separated from the reacting mixture. To rapidly remove the water formed in the reaction, the reaction mixture must be maintained at a sufficiently high temperature and under a sufficiently low pressure. It is desired to maintain the water in the reaction mixture at a low level so that no undissolved free water is present in the reacting mixture.

The process will be described in relation to the FIGURE. In the FIGURE, vessel 1 is a vessel for preparing a slurry of a hydrous saccharide source in a fatty alcohol. A predetermined amount of fatty alcohol is introduced into vessel 1 through line 2. The fatty alcohol is generally at a temperature in the range of from about 20° C. to about 50° C. The agitation means 7 having rotating impeller 8 is placed in motion after the required amount of fatty alcohol has been introduced into vessel 1.

The fatty alcohol in vessel 1 is circulated in the vessel through line 9, pump 12 and line 13. Vessel 3 is a hydrous saccharide source storage zone. A predetermined amount of the hydrous saccharide source is introduced into storage zone 3. After the alcohol has been introduced into vessel 1 and the mixing means 7 and circulating pump 12 have been placed in operation, the hydrous saccharide source is introduced into vessel 1 through line 4, valve means 5 which can be a star feeder valve or its equivalent and line 6 into the fatty alcohol in vessel 1.

Mixing means 7 can be a high shear mixer, an agitator or other means which provides a suspension of finely divided hydrous saccharide source in a first portion of fatty alcohol. Vessel 1 can have heating and cooling means or have a heat exchange means in line 13 between pump 12 and vessel 1. Heat exchange means in line 13 or associated with vessel 1 are not shown. However, it would be well known to one skilled in the art that a jacket or coils could be welded to the external surfaces of vessel 1 or a shell and tube heat exchanger included in line 13 to provide heating or cooling to the slurry of the hydrous saccharide source in the first portion of fatty alcohol. The slurry of the hydrous saccharide source in the first portion of fatty alcohol is agitated by mixing means 7 and circulated by means of circulating pump means 12 to maintain the solid hydrous saccharide source suspended in the first portion of fatty alcohol.

A second portion of fatty alcohol is introduced into dehydration and reaction vessel 22. The second portion of the fatty alcohol can be hot fatty alcohol which has been recovered from a previous reaction sequence or virgin alcohol which has been heated to an elevated temperature or a combination thereof. The second portion of the fatty alcohol can be heated by circulation of the fatty alcohol through line 24, pump means 27, line 28, heat exchanger 29, line 32, valve 35 and line 36. The dehydration and reaction vessel 22 can also have a heating jacket or heating coils affixed to the sides and bottom of the vessel (not shown). When the second portion of the fatty alcohol has been introduced into vessel 22, the mixing means 25 is activated and mixing elements 26 rotated in the vessel. The mixing means 25 and pumping means are useful to prevent the finely divided hydrous or anhydrous saccharide particles from settling in the vessel and to permit rapid removal of water from the mixture.

After the second portion of the fatty alcohol has been heated to the required temperature and the pressure in vessel 22 has been reduced to the required pressure through line 37 to the vacuum system (not shown), a controlled stream of the slurry of hydrous source of saccharide is introduced into dehydration and reaction vessel 22 through line 14, flow control means 15, and line 16. The slurry of the hydrous saccharide source in the first portion of fatty alcohol is introduced into suction line 24 of pump 27 and is circulated through heat exchanger 29 to dehydration and reaction vessel 22.

The temperature in the reaction vessel is maintained at the desired level (generally below about 110° C.) by controlling the heat introduced into the second portion of the fatty alcohol by heat exchanger 29 or any other heating means in the system and the rate at which the slurry of the hydrous saccharide source in the first portion of the fatty alcohol is introduced into vessel 22. The temperature of the mixture is maintained at a temperature sufficiently high to remove at least a portion of the water associated with the hydrous saccharide source but below a temperature at which the hydrous saccharide source melts or forms a syrup before water is removed. As water is removed the temperature can be ramped when the saccharide source tends to liquify at elevated temperature.

After all of the slurry of the hydrous saccharide source in the first portion of the fatty alcohol has been introduced into dehydration and reaction vessel 22, the temperature of the mixture of the first portion and the second portion of the fatty alcohol and the saccharide source is maintained at or rapidly raised to the temperature at which catalyst is to be added. The pressure in the vessel is maintained at a low level and any remaining water associated with the hydrous saccharide source is removed. The reduced pressure which can be maintained in dehydration and reaction vessel 22 is dependent upon the fatty alcohol to be reacted and the capabilities of the vacuum producing system. Since the reaction is to be carried out at a temperature in the range of from about 90° C. to about 140° C., preferably 95° C. to 130° C., the reduced pressure which can be maintained on a $C_7$ alcohol is higher than one which can be maintained when a $C_{22}$ fatty alcohol is utilized as the reactant. The pressure must be as low as possible without boiling a substantial amount of the fatty alcohol from the reaction mixture.

After the amount of water in the mixture has been reduced to the required level, an acid catalyst in vessel 17 is introduced into the mixture of saccharide and fatty alcohol through line 18, valve means 19 and line 23 into the suction line 24 of pump 27. The acid catalyst is introduced into the circulating slurry of saccharide source in fatty alcohol at a rate such that the concentration of the acid catalyst in the fatty alcohol slurry in the catalyst addition zone remains low.

If the mixture of fatty alcohol and saccharide source is at the required temperature, as soon as the acid catalyst is introduced into the mixture, the fatty alcohol begins reacting with the saccharide source to form the aliphatic glycoside. With aqueous solutions of polar catalysts a temperature lower than reaction temperature is selected for catalyst addition. After catalyst addition, the temperature is raised to promote the desired reaction rate.

As is well known in the art, the acetalization of the saccharide source with the fatty alcohol produces water. The water is removed from the reacting mixture substantially as soon as it is formed due to the elevated temperature and the reduced pressure maintained on the reacting mixture. The mixture of the saccharide source and the fatty alcohol is reacted for from about 1 to about 15 hours after the acid catalyst has been introduced into the mixture. The reaction is carried out until the amount of unreacted saccharide source in the mixture has reached a predetermined level. Generally, the amount of unreacted saccharide source in the reaction mixture is less than about 5% by weight of the alkyl glycoside formed and preferably less than about 2% by weight of the glycoside formed and most preferably less than 0.25% by weight of the aliphatic glycoside formed.

After the reaction has been substantially completed, the reaction mixture can be cooled by circulating the reaction mixture through line 24, circulating pump 27, line 28, heat exchange means 29 which now becomes a reaction product cooling means, line 32, valve 35 and line 36.

After the reaction mixture has been cooled to a predetermined temperature, the reaction mixture can be removed from vessel 22 by closing valve 35 in line 32 and opening valve 34 in line 33 and pumping the mixture to the product recovery portion of the process for further treatment.

In an alternative method, after the reaction mixture has been reduced to the required residual saccharide content, a neutralizing material such as an alkali metal hydroxide, alkali earth metal oxide or alkali earth metal hydroxide can be added to vessel 22 to neutralize the acid catalyst. As is well known in the art, the neutralized mixture is then passed to a means for separating the unreacted fatty alcohol to recover the aliphatic glycoside and the aliphatic glycoside can be mixed with water and/or further treated to reduce the color, stabilize the color and dilute the material to the concentration at which it is to be sold. Generally the aliphatic glycosides are sold as aqueous mixtures containing from about 30% to about 80% by weight of the active surfactant material.

The method of the present invention has been described by way of the FIGURE. However, there are many ways that the method can be carried out. The important parameters of the process are the formation of a slurry of a hydrous source of reducing saccharide in a first portion of fatty alcohol, introducing the slurry of the hydrous saccharide source in the first portion of the fatty alcohol into a heated second portion of the fatty alcohol under reduced pressure, at a controlled rate, maintaining the mixture of the first portion of the fatty alcohol containing the hydrous source of saccharide and the second portion of fatty alcohol at an elevated temperature and reduced pressure to remove the water from the hydrous saccharide source. The temperature is generally maintained at a level such that water can be removed from the mixture but the hydrous saccharide source does not liquify. An acid catalyst is introduced into the mixture of fatty alcohol and saccharide source after its water content has been reduced to a desired level and the temperature raised to, or maintained in, the range for reaction between the alcohol and saccharide source. The mixture is reacted at an elevated temperature and reduced pressure to form the aliphatic glycoside.

The aliphatic glycoside containing mixture is generally further treated to neutralize the acid catalyst, separate the excess or unreacted fatty alcohol from the aliphatic glycoside product, mix with water, reduce the level of color of the product, stabilize the color and adjust the concentration of the aliphatic glycoside to the concentration and pH level at which it is sold.

The acid can be neutralized with alkali metal hydroxides, alkaline earth metal oxides or hydroxides, aluminum hydroxide or oxide or mixtures thereof. The unreacted fatty alcohol can be separated from the aliphatic glycoside product by solvent extraction, low pressure evaporation such as in a thin film evaporator, wiped film evaporator and the like. The product can be treated to reduce and stabilize the color before or after separation of the fatty alcohol from the neutralized reaction mixture. Preferably the fatty alcohol is removed from the product before the product is treated to reduce and stabilize the color. The color level can be reduced by known oxidation means such as hypochlorite bleaching, peroxide bleaching, ozone treatment, alkali metal borohydride addition and the like.

We claim:

1. In a process for preparing aliphatic glycosides of the formula

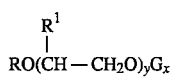

wherein R is the residue of a fatty alcohol having from about 7 to about 22 carbon atoms which can be saturated or unsaturated, straight chain or branched, $R^1$ is hydrogen, $CH_3$, or $CH_2-CH_3$, G is the residue of a reducing saccharide, y is a number of from 0 to about 5, and x is a number of from 1 to about 5, by reacting an alcohol of the formula

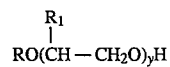

with a source of reducing saccharide in the presence of an acid catalyst and a stoichiometric excess of fatty alcohol under reduced pressure at a temperature in the range of about 90° C. to about 140° C. to form a reaction mixture containing the aliphatic glycoside and recovering the aliphatic glycoside from the reaction mixture, the improvement which comprises:

a) mixing a hydrous saccharide source with a first portion of the alcohol to form a mixture;

b) continuously introducing the mixture of the first portion of alcohol and hydrous saccharide source, in a controlled stream, into a heated second portion of the alcohol wherein the first portion of alcohol is less than 50% by weight of the total weight of the first and second portions of alcohol;

c) heating the mixture under a reduced pressure to remove water and form a mixture of alcohol and saccharide source with a reduced water content;

d) introducing the acid catalyst into the heated mixture of alcohol and saccharide source with reduced water content and;

e) reacting the alcohol with the saccharide source to form a reaction mixture containing the aliphatic glycoside.

2. A process of claim 1 wherein the hydrous saccharide source is dextrose monohydrate.

3. A process of claim 2 wherein y is zero, x is a number from 1 to about 2.5, the alcohol is at least one aliphatic alcohol having from 7 to about 18 carbon atoms, the temperature of the second portion of alcohol is maintained at a temperature between about 60° C. and 110° C. and a pressure from about 5 mm Hg to about 100 mm Hg during the addition of the mixture of the hydrous saccharide source in the first portion of alcohol and reacting the mixture at a temperature of from about 100° C. to about 125° C. and a pressure of from about 5 mm Hg to about 100 mm Hg in the presence of at least one catalyst selected from the group consisting of an acid form of a surfactant and paratoluene sulfonic acid and from about 2 moles of alcohol to about 6 moles of alcohol per mole of reducing saccharide residue.

4. A process of claim 1 wherein the alcohol and saccharide source are related at a temperature of from 100° C. to 130° C.

5. A process of claim 4 wherein the alcohol and saccharide source are reacted at a temperature of from 100° C. to about 120° C.

6. A process of claim 1 wherein the acid catalyst comprises at least one member selected from the group consisting of paratoluene sulfonic acid, sulfosuccinic acid, an acid form of a surfactant, sulfuric acid, trifluoroacetic acid, alkyl esters of sulfosuccinic acid, sulfonated fatty acid, sulfonated fatty acid esters and acidic ion exchange resin.

7. A process of claim 1 wherein the mixture containing the hydrous saccharide source and second portion of alcohol are maintained at a temperature below about 110° C. and a pressure below about 100 mm Hg until a major portion of the water associated with the hydrous saccharide source has been removed from the mixture.

8. A process of claim 1 wherein the fatty alcohol is an alcohol having from about 8 to about 18 carbon atoms.

9. A process of claim 8 wherein the alcohol is a straight chain alcohol.

10. A process of claim 1 wherein the first portion of alcohol is from about 20% to about 40% by weight of the amount of the first and second portions of alcohol.

11. A process of claim 1 wherein y is zero and x is a number of from 1 to about 2.5.

12. A process of claim 1 wherein the second portion of fatty alcohol is maintained at a temperature of from about 60° C. to about 110° C. during mixing of the hydrous saccharide source with the first portion of alcohol.

13. A method for producing a substantially dry mixture of a saccharide source and a fatty alcohol containing from 7 to 22 carbon atoms comprising:

a) forming a slurry of a hydrous saccharide source in a first portion of the fatty alcohol;

b) heating a second portion of the fatty alcohol to a temperature of from about 60° C. to 110° C. under a pressure of less than about 100 mm Hg;

c) continuously introducing the slurry of the hydrous saccharide source in the first portion of fatty alcohol into the second portion of fatty alcohol to form a mixture wherein the first portion of fatty alcohol is less than 50% by weight of the total weight of the first and second portions of the fatty alcohol while maintaining the temperature of the mixture between about 60° C. and 110° C. and a pressure of less than about 100 mm Hg; and d) adjusting the temperature of the mixture to a range of from about 95° C. to about 125° C. if the temperature is below this range and maintaining the pressure at less than 100 mm Hg to form a substantially anhydrous mixture.

14. A method of claim 13 wherein the first portion of alcohol is from about 20% to about 40% of the amount of the first and second portions of alcohol.

15. A method of claim 13 wherein the pressure is from about 5 mm Hg to about 50 mm Hg.

* * * * *